United States Patent
Feldman

(10) Patent No.: US 6,937,343 B2
(45) Date of Patent: Aug. 30, 2005

(54) LASER SCANNER WITH AMPLITUDE AND PHASE DETECTION

(75) Inventor: Haim Feldman, Nof Ayalon (IL)

(73) Assignee: Applied Materials, Israel, Ltd., Rehovot (IL)

( * ) Notice: Subject to any disclaimer, the term of this patent is extended or adjusted under 35 U.S.C. 154(b) by 266 days.

(21) Appl. No.: 10/232,093

(22) Filed: Aug. 29, 2002

(65) Prior Publication Data

US 2004/0042014 A1 Mar. 4, 2004

(51) Int. Cl.[7] .................................................. G01B 9/02
(52) U.S. Cl. ........................................................ 356/484
(58) Field of Search ................................ 356/484, 485, 356/486, 487, 488, 489

(56) References Cited

U.S. PATENT DOCUMENTS 6,052,478 A    4/2000 Wihl et al.
6,118,518 A * 9/2000 Hobbs ........................ 356/4.09

OTHER PUBLICATIONS

Anthony Vanderlught, *Optical Signal Processing*, John Wiley & Sons, New York, 1992, Chapters 9–10.

* cited by examiner

*Primary Examiner*—Andrew H. Lee
(74) *Attorney, Agent, or Firm*—Blakely, Sokoloff, Taylor & Zafman

(57) ABSTRACT

A method for optical evaluation of a sample includes scanning a beam of coherent radiation over the sample, whereby the radiation is scattered from the sample, while directing a portion of the scanning beam toward a diffraction grating so that the portion of the beam is scanned over the grating, whereby a frequency-shifted reference beam is diffracted from the grating. The scattered radiation and the frequency-shifted reference beam are combined at a detector to generate an optical heterodyne signal.

16 Claims, 3 Drawing Sheets

LASER SCANNER WITH AMPLITUDE AND PHASE DETECTION

FIELD OF THE INVENTION

The present invention relates generally to laser scanning systems, and specifically to methods and systems for optical inspection of substrates based on laser scanning.

BACKGROUND OF THE INVENTION

Heterodyne detection is a well-known method of optical signal processing. It is described, for example, by Vanderlugt in *Optical Signal Processing* (John Wiley & Sons, New York, 1992), Chapters 9–10, which are incorporated herein by reference. Typically, to perform heterodyne detection, a laser beam is split into a probe beam and a reference beam. The reference beam, of amplitude $A_0$, is frequency-shifted by a known carrier frequency $f_c$, typically using an acousto-optic modulator operating in the radio frequency (RF) range. The probe beam is incident on the sample, and is modified in amplitude and phase as a result, so that the beam reflected (or transmitted) by the sample has amplitude $A_1(t)$ and phase $\phi(t)$. The probe and reference beams are recombined and mutually interfere to give an optical signal whose intensity has the form:

$$I(t)=A_0^2+A_1^2(t)+2A_0A_1(t)\cos[2\pi f_c t-\phi(t)] \qquad (1)$$

This combined signal is incident on a detector, and the detector output is filtered to extract the signal component at frequency $f_c$. This heterodyne component is linear in the amplitude change $A_1(t)$ caused by the sample, and also contains the phase change data $\phi(t)$. Therefore, information regarding the structure and characteristics of the sample is typically more easily extracted from the heterodyne signal than from simple (homodyne) intensity-based detection.

Interferometric measurements are known in the art of optical inspection of patterned substrates, such as semiconductor wafers. For example, U.S. Pat. No. 6,052,478, whose disclosure is incorporated herein by reference, describes an automated photomask inspection apparatus that uses transmitted or reflected interferometry to measure phase shifts produced by such masks. Variations in the phase shifts are indicative of defects due to undesired thickness variations in the photomask.

SUMMARY OF THE INVENTION

It is an object of some aspects of the present invention to provide laser scanning systems that can be used to provide information regarding both the reflectivity of a sample and phase variations induced by the sample surface.

It is a further object of some aspects of the present invention to provide an improved laser scanning system for use in heterodyne detection.

In some preferred embodiments of the present invention, a scanning laser beam is split into probe and reference beams. The probe beam is focused onto the surface of a sample, such as a semiconductor wafer, while the reference beam is focused to a small spot on a grating. As the laser beam is scanned across the sample, it simultaneously scans across the surface of the grating, causing the reference beam to be diffracted from the grating with a phase shift that varies over time as the beam is scanned. This time-varying phase shift is equivalent to modulating the reference beam at a frequency that is proportional to the scanning speed and grating pitch. The probe beam scattered from the sample is combined with the frequency-modulated reference beam at a detector. The amplitude of the resultant heterodyne signal is indicative of the reflectivity of the sample, while variations in the phase of the heterodyne signal represent phase changes caused by the sample in the scattered probe beam.

Thus, preferred embodiments of the present invention allow heterodyne detection to be implemented simply in a laser scanning system, without requiring an active modulator to modulate the reference beam. Instead, the same scanning device that is used to scan the probe beam across the sample also provides the means for modulating the reference beam, using only a passive, stationary grating and associated optics.

In other preferred embodiments of the present invention, a homodyne detection scheme is used to measure the reflectivity and phase characteristics of the sample. In this case, the reference beam is reflected from a planar mirror before being combined with the probe beam scattered from the sample. The combined beam is split into phase and quadrature components, preferably by means of suitable beam retardation and polarization optics. The time-varying amplitudes of the phase and quadrature beam components are measured by respective detectors, while the probe beam scans over the sample. The phase and quadrature signals output by the detectors are then processed together in order to separate the amplitude (reflectivity-related) and phase information carried by the scattered beam.

There is therefore provided, in accordance with a preferred embodiment of the present invention, a method for optical evaluation of a sample, including:

scanning a beam of coherent radiation over the sample, whereby the radiation is scattered from the sample;

directing a portion of the scanning beam toward a diffraction grating so that the portion of the beam is scanned over the grating, causing a frequency-shifted reference beam to be diffracted from the grating; and combining the scattered radiation and the frequency-shifted reference beam at a detector to generate an optical heterodyne signal.

Preferably, scanning the beam includes scanning the beam laterally with a predetermined scanning speed, causing the reference beam to be shifted by a carrier frequency that is proportional to the scanning speed. Further preferably, the grating has a predetermined pitch, causing the reference beam to be shifted by a carrier frequency that is proportional to the pitch of the grating.

In a preferred embodiment, the diffraction grating includes a Littrow grating, and directing the portion of the scanning beam toward the diffraction grating includes directing the portion of the scanning beam toward the Littrow grating along a predetermined beam direction, so that the grating returns the frequency-shifted reference beam substantially parallel to the predetermined beam direction. In a further preferred embodiment, directing the portion of the scanning beam toward the diffraction grating includes dividing the portion of the scanning beam into multiple diffraction orders, including a zero order, and directing one of the diffraction orders other than the zero order toward the diffraction grating.

Preferably, the method includes detecting and processing the optical heterodyne signal responsive to a known carrier frequency of the reference beam, so as to derive amplitude and phase information from the scattered radiation. Most preferably, processing the optical heterodyne signal includes processing the amplitude and phase information to determine a property of a surface of the sample from which the radiation is scattered. In a preferred embodiment, the sample includes a semiconductor wafer, and processing the amplitude and phase information includes processing the information to detect a defect on the surface of the wafer.

There is also provided, in accordance with a preferred embodiment of the present invention, apparatus for optical evaluation of a sample, including:

a radiation detector, adapted to detect an optical heterodyne signal;

a scanner, adapted to scan a beam of coherent radiation over the sample, whereby the radiation is scattered from the sample;

a diffraction grating;

a beamsplitter, aligned with the scanned beam so as to direct a portion of the beam toward the diffraction grating so that the portion of the beam is scanned over the grating, causing a frequency-shifted reference beam to be diffracted from the grating; and collection optics, positioned to combine the scattered radiation and the frequency-shifted reference beam to generate the optical heterodyne signal at the detector.

Preferably, the apparatus includes a signal processor, coupled to detect and process the optical heterodyne signal responsive to a known carrier frequency of the reference beam, so as to derive amplitude and phase information from the scattered radiation.

There is additionally provided, in accordance with a preferred embodiment of the present invention, a method for optical evaluation of a sample, including:

scanning a beam of coherent radiation over the sample, whereby the radiation is scattered from the sample;

splitting off a portion of the beam to serve as a reference beam;

combining the scattered radiation and the reference beam so as to generate a combined beam that is characterized by interference between the scattered radiation and the reference beam;

separating the combined beam into first and second beam components having a predetermined phase difference therebetween; and comparing respective time variations of the first and second beam components so as to derive amplitude and phase information from the scattered radiation.

Preferably, separating the combined beam includes splitting the combined beam into phase and quadrature components.

There is further provided, in accordance with a preferred embodiment of the present invention, apparatus for optical evaluation of a sample, including:

a scanner, adapted to scan a beam of coherent radiation over the sample, whereby the radiation is scattered from the sample;

a first beamsplitter, aligned with the scanned beam so as to separate off a portion of the beam to form a reference beam, which is not scattered from the sample;

collection optics, positioned to combine the scattered radiation and the reference beam so as to generate a combined beam that is characterized by interference between the scattered radiation and the reference beam;

a second beamsplitter, operative to separate the combined beam into first and second beam components having a predetermined phase difference therebetween;

first and second detectors, positioned to receive the first and second components, respectively, and adapted to generate first and second signals responsive thereto; and a signal processor, which is coupled to receive the first and second signals and to compare respective time variations of the signals so as to derive amplitude and phase information regarding the scattered radiation.

The present invention will be more fully understood from the following detailed description of the preferred embodiments thereof, taken together with the drawings in which:

DETAILED DESCRIPTION OF A PREFERRED EMBODIMENT

Figure 1:
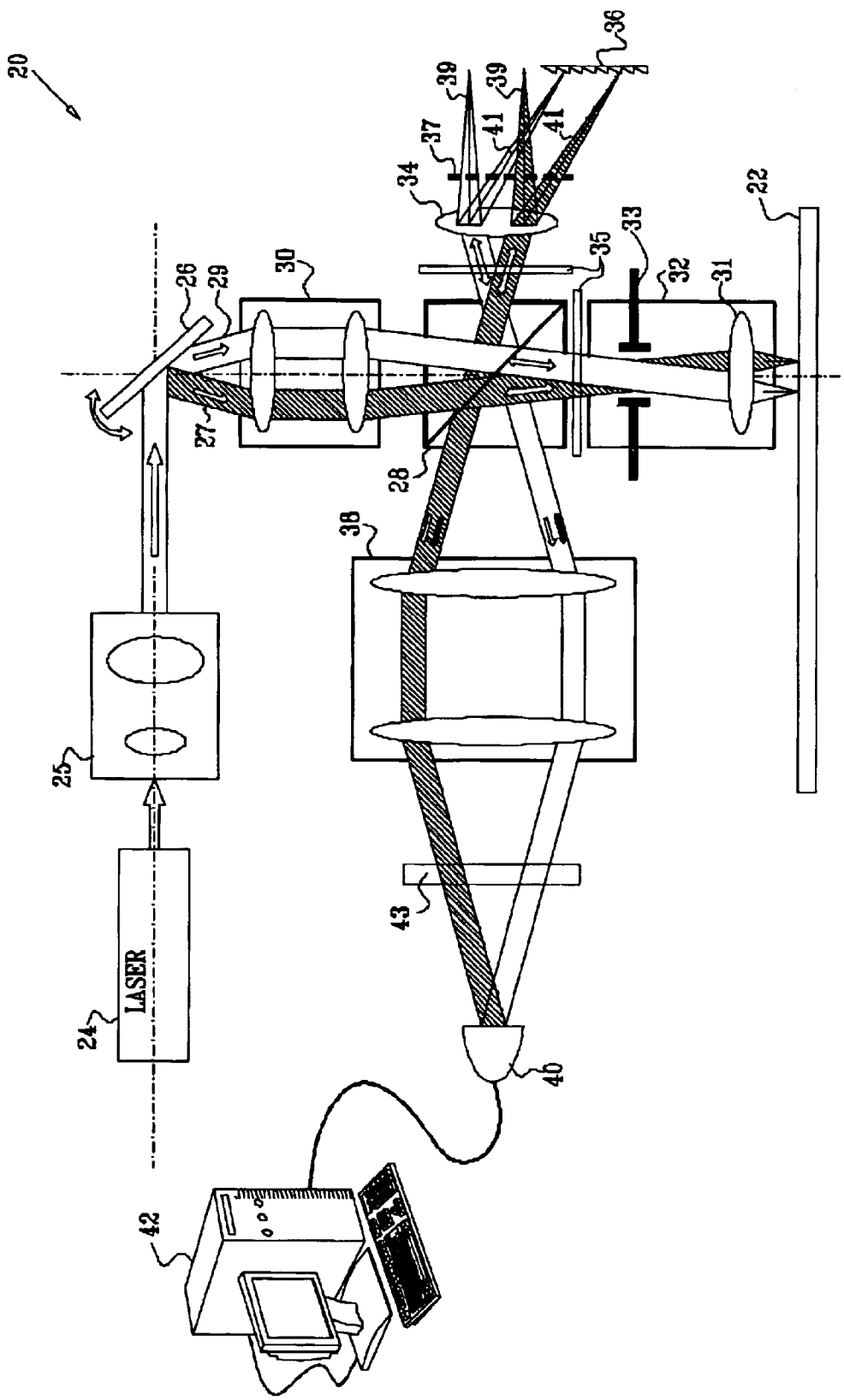
FIG. 1 is a schematic side view of a laser scanner system with heterodyne detection, in accordance with a preferred embodiment of the present invention.

FIG. 1 is a schematic side view of a system 20 for laser scanning of a substrate 22, in accordance with a preferred embodiment of the present invention. Typically, substrate 22 comprises a semiconductor wafer, which is scanned by system 20 in order to detect defects on the wafer surface. Alternatively, the principles embodied in the system may be applied to other fields of optical inspection. A laser 24 generates a beam of coherent light, which is expanded by a beam expander 25 and is rapidly deflected by a scanner 26, such as an acousto-optic scanner, galvanometer-based scanner or rotating polygonal mirror, as is known in the art. Scanner 26 preferably scans the laser beam at high angular speed, typically covering a range of about 100 mrad (milliradians) in a scan time on the order of 25 $\mu$s. Two beams 27 and 29 are shown reflected from scanner 26, representing approximately the beam positions at the extremes of the scan.

The scanned laser beam is focused by an input telescope 30 and is then split by a beamsplitter 28 into probe and reference beams. The probe beam is focused by a probe objective assembly 32 onto the surface of substrate 22. The objective assembly preferably comprises an objective lens 31 with a telecentering stop 33, used to maintain uniformity of the focal spot on substrate 22 over the entire scan line. Telescope 30 is preferably configured to image the pivot point of the beam at scanner 26 onto stop 33.

Light scattered from the surface is collected by objective assembly 32 and is directed back toward beamsplitter 28. As the beam scans over the surface of the substrate, the amplitude of the scattered light is modulated by the varying reflectivity of the substrate. The phase of the scattered light also varies, due to microscopic variations in the composition and elevation of the surface. These amplitude and phase variations may occur due to features intentionally formed on the surface, such as patterns that are deposited on semiconductor wafers in the course of integrated circuit manufacture, or due to defects.

The reference beam is focused by a reference objective 34 onto a first diffraction grating 37. This first grating is positioned and blazed so that a zero order 39 of the grating is discarded, while a first order 41 is incident on a second diffraction grating 36. The second grating is preferably a Littrow grating operating in first order. Second grating 36 is blazed and aligned so that the first-order light that it diffracts is directed back toward first grating 37, which then diffracts this light toward beamsplitter 28 parallel to the incident reference beam. Scanner 26 causes the reference beam to scan across the surface of the grating (vertically in the view shown in the figures), with the result that the diffracted beam is frequency-shifted at a carrier frequency $f_c$. The frequency shifting mechanism is described in detail below with reference to FIG. 2.

Preferably, beamsplitter 28 is a polarizing beamsplitter, causing the reference beam (reflected toward the right) to be P-polarized, while the probe beam (passing through the beamsplitter) is S-polarized. Typically, the beam emitted by laser 24 is linearly polarized, and the beam polarization is oriented relative to beamsplitter 28 so that most of the beam power passes to the probe beam. (Alternatively, a non-polarizing beamsplitter may be used, though at the expense of lower efficiency.) The polarized probe and reference beams pass through respective quarter-wave plates 35 on both their forward and return paths. In consequence, the returned probe beam becomes P-polarized, so that it passes directly through beamsplitter 28, while the returned reference beam becomes S-polarized, so that it is reflected to the left by the beamsplitter.

An output telescope 38 focuses both the scattered probe beam and the diffracted reference beam onto a detector 40, causing the beams to interfere at the detector. If the probe and reference beams are orthogonally polarized, as described above, a polarizer 43, oriented at 45° between the S and P polarization directions, is interposed in front of detector 40 in order to engender the desired interference. Telescope 38 is preferably configured to image stop 33 onto detector 40. On account of the modulation of the reference beam, the signal received by detector 40 has a heterodyne component at the carrier frequency $f_c$, as given above by equation (1). A signal processor 42, typically a general-purpose computer with suitable front-end electronics, filters and analyzes the heterodyne signal component, in order to measure the amplitude and phase variations created in the probe beam due to features and defects on the surface of the sample.

Figure 2:
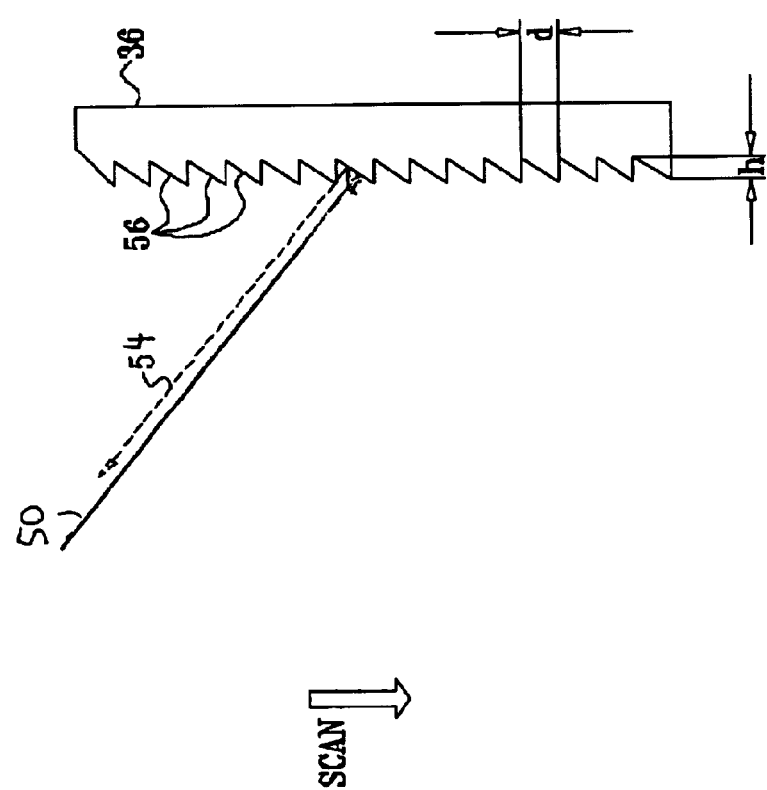
FIG. 2 is a schematic detail view of a grating used in the system of FIG. 1.

FIG. 2 is a schematic detail view of grating 36, showing how an incident reference beam 50 is frequency-modulated by scanning across the grating. As shown in the figure, grating 36 is preferably a Littrow grating, which is blazed so as to reflect a first-order beam 54 at the specified laser wavelength, parallel to the incident beam. Alternatively, the grating may be configured so that a second- or higher-order beam is diffracted back parallel to the incident beam. Other grating types and geometries may be used, as well. For example, system 20 may be configured in the form of a Mach-Zehnder interferometer, as is known in the art, in which case grating 36 may be replaced by a transmissive grating, or another type of reflective diffraction grating may be used. In such cases, the diffracted beam is not necessarily parallel to the incident beam over its entire path as in the present embodiment.

In the embodiment shown in FIG. 2, the front surface of grating 36 comprises parallel teeth 56 with a grating period d and a blaze height h. To provide the required constructive interference in first-order beam 54, the blaze height is equal to one-half wave at the laser wavelength. Thus, as the incident reference beam scans over the grating surface by a distance d, the phase of the first-order beam varies cyclically through $2\pi$. Assuming the incident beam scans over the surface at a linear velocity v, the modulation frequency of the first-order beam is simply $f_c=v/d$, i.e., the number of teeth 56 traversed in one second.

For effective extraction of information regarding substrate 22 from the heterodyne signal by processor 42, it is desirable that $f_c$ be substantially greater than the information bandwidth. Assuming reference objective 34 to have focal length L, the modulation frequency as a function of the parameters of scanner 26 and grating 36 is given by:

$$f_c = \frac{\text{scan\_angle}}{\text{scan\_time}} \cdot \frac{L}{d} \tag{2}$$

For L=50 mm, with a scan angle of 100 mrad, scan time 25 $\mu$s, and d=2 $\mu$m (grating pitch 500 line pairs/mm), $f_c$=100 MHz. This frequency is sufficient for use in high-speed wafer inspection systems, for example, which typically scan wafers at rates on the order of tens of millions of spots per second.

Figure 3:
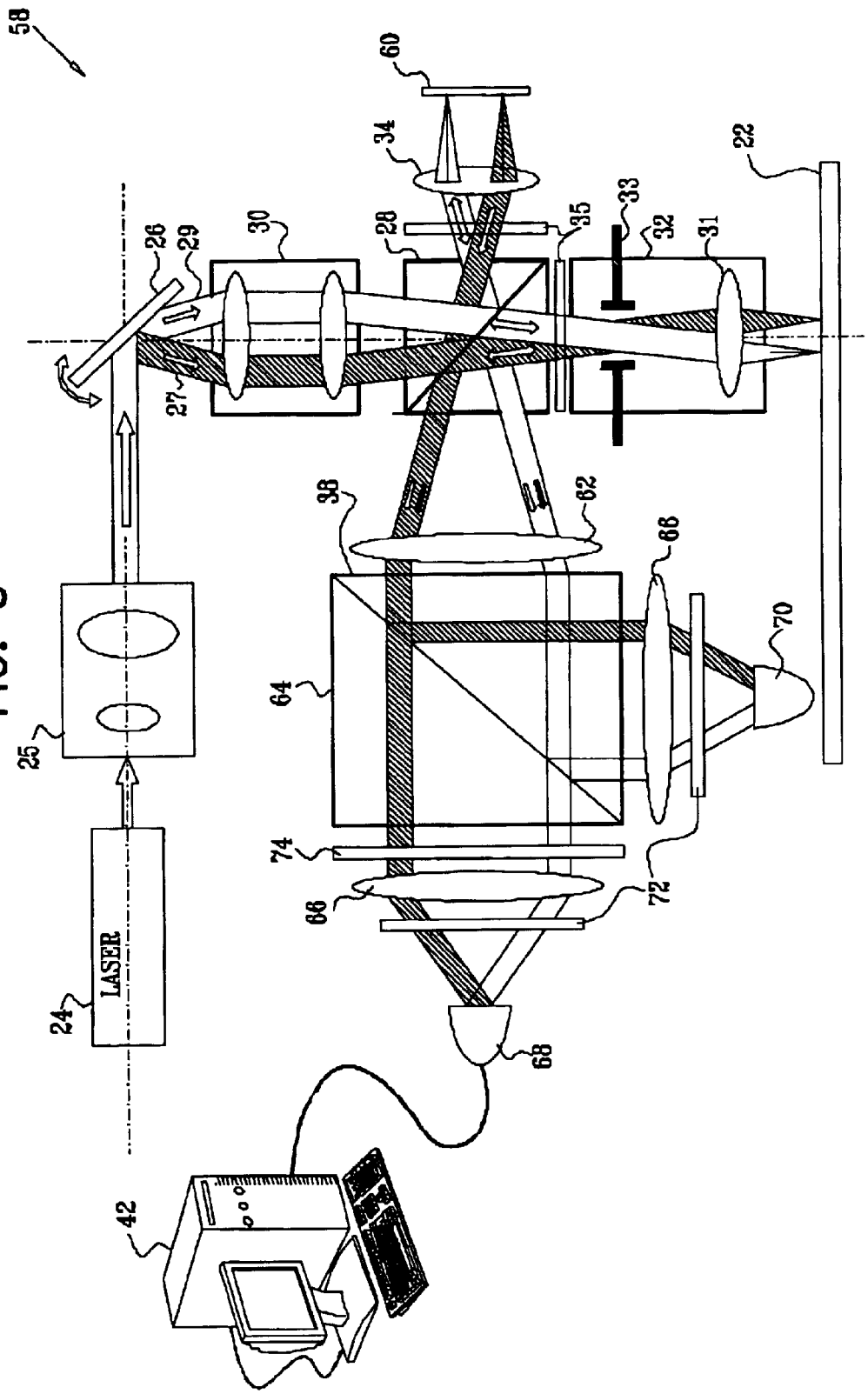
FIG. 3 is a schematic side view of a laser scanner system with homodyne detection, in accordance with a preferred embodiment of the present invention.

FIG. 3 is a schematic side view of a system 58 for laser scanning of substrate 22, in accordance with another preferred embodiment of the present invention. System 58 is similar in certain aspects to system 20, as shown and described above, except that system 58 operates by homodyne, rather than heterodyne, detection. The reference beam split off by beamsplitter 28 is focused by objective 34 onto a planar mirror 60, which thus reflects the reference beam back upon itself with constant phase delay. An output lens 62 collects both the scattered probe beam and the diffracted reference beam into a detection beamsplitter 64. Focusing lenses 66 direct the probe and reference beams from beamsplitter 64 together onto detectors 68 and 70, so that the beams interfere at the detectors.

As described above with reference to FIG. 1, the probe and reference beams are preferably orthogonally polarized. Therefore, polarizers 72, oriented at 45° relative to the S and P polarization directions, are interposed in the paths of the beams following beamsplitter 64, so as to engender interference between the beams. Alternatively, if beamsplitter 64 is a polarizing beamsplitter, with its polarization axis oriented at 45° relative to the S and P directions of the probe and reference beams, polarizers 72 may be eliminated.

A quarter-wave plate 74 is inserted in the beam path to detector 68. Plate 74 has the effect of shifting the relative phases of the S and P beams by 90°, so that the interfering beams at one of detectors 68 and 70 are "in phase," while the interfering beams at the other detector are in "quadrature." (For convenience, it will be assumed that the in-phase component is incident on detector 68, while the quadrature component is incident on detector 70, but these designations are arbitrary.) The in-phase signal output by detector 68 can then be expressed as:

$$I(t)=A_0^2+A_1^2(t)+2A_0A_1(t)\cos[\phi(t)] \tag{3}$$

while the quadrature signal output by detector 70 is:

$$Q(t)=A_0^2+A_1^2(t)+2A_0A_1(t)\sin[\phi(t)] \tag{4}$$

By comparing these two signals, processor 42 is able to separate the amplitude component $A_1(t)$ and the phase component $\phi(t)$ of the interfering beams. These components are indicative of the amplitude and phase variations created in the probe beam due to features and defects on the surface of the sample.

Although the preferred embodiments described above are directed to bright field detection of light reflected from a sample, the principles of the present invention may be applied, mutatis mutandis, to dark field detection schemes, as well as to transmission-based measurements. In dark field inspection with heterodyne detection, for example, a two-dimensional, non-Littrow grating can be used to generate the frequency-shifted reference beam at desired angles. These various detection schemes are useful not only in observing defects and pattern variations in semiconductor wafers and photomasks, but also in a wide range of other applications of optical heterodyne and homodyne detection, such as in scanning microscopy, including particularly confocal microscopy.

It will thus be appreciated that the preferred embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

What is claimed is:

1. A method for optical evaluation of a sample, comprising:

scanning a beam of coherent radiation over the sample, whereby the radiation is scattered from the sample;

directing a portion of the scanning beam toward a diffraction grating so that the portion of the beam is scanned over the grating, whereby a frequency-shifted reference beam is diffracted from the grating; and combining the scattered radiation and the frequency-shifted reference beam at a detector to generate an optical heterodyne signal.

2. A method according to claim 1, wherein scanning the beam comprises scanning the beam laterally with a predetermined scanning speed, causing the reference beam to be shifted by a carrier frequency that is proportional to the scanning speed.

3. A method according to claim 1, wherein the grating has a predetermined pitch, causing the reference beam to be shifted by a carrier frequency that is proportional to the pitch of the grating.

4. A method according to claim 1, wherein the diffraction grating comprises a Littrow grating, and wherein directing the portion of the scanning beam toward the diffraction grating comprises directing the portion of the scanning beam toward the Littrow grating along a predetermined beam direction, so that the grating returns the frequency-shifted reference beam substantially parallel to the predetermined beam direction.

5. A method according to claim 1, wherein directing the portion of the scanning beam toward the diffraction grating comprises dividing the portion of the scanning beam into multiple diffraction orders, including a zero order, and directing one of the diffraction orders other than the zero order toward the diffraction grating.

6. A method according to claim 1, and comprising detecting and processing the optical heterodyne signal responsive to a known carrier frequency of the reference beam, so as to derive amplitude and phase information from the scattered radiation.

7. A method according to claim 6, wherein processing the optical heterodyne signal comprises processing the amplitude and phase information to determine a property of a surface of the sample from which the radiation is scattered.

8. A method according to claim 7, wherein the sample comprises a semiconductor wafer, and wherein processing the amplitude and phase information comprises processing the information to detect a defect on the surface of the wafer.

9. Apparatus for optical evaluation of a sample, comprising:

a radiation detector, adapted to detect an optical heterodyne signal;

a scanner, adapted to scan a beam of coherent radiation over the sample, whereby the radiation is scattered from the sample;

a diffraction grating;

a beamsplitter, aligned with the scanned beam so as to direct a portion of the beam toward the diffraction grating so that the portion of the beam is scanned over the grating, causing a frequency-shifted reference beam to be diffracted from the grating; and collection optics, positioned to combine the scattered radiation and the frequency-shifted reference beam to generate the optical heterodyne signal at the detector.

10. Apparatus according to claim 9, wherein the scanner is adapted to scan the beam laterally with a predetermined scanning speed, causing the reference beam to be shifted by a carrier frequency that is proportional to the scanning speed.

11. Apparatus according to claim 9, wherein the diffraction grating has a predetermined pitch, causing the reference beam to be shifted by a carrier frequency that is proportional to the pitch of the grating.

12. Apparatus according to claim 9, wherein the diffraction grating comprises a Littrow grating, and wherein the beamsplitter is aligned so as to direct the portion of the scanning beam toward the Littrow grating along a predetermined beam direction so that the grating returns the frequency-shifted reference beam substantially parallel to the predetermined beam direction.

13. Apparatus according to claim 9, and comprising a further diffractive element, which is operative to divide the portion of the scanning beam into multiple diffraction orders, including a zero order, and to direct one of the diffraction orders other than the zero order toward the diffraction grating.

14. Apparatus according to claim 9, and comprising a signal processor, coupled to detect and process the optical heterodyne signal responsive to a known carrier frequency of the reference beam, so as to derive amplitude and phase information from the scattered radiation.

15. Apparatus according to claim 14, wherein the signal processor is adapted to process the amplitude and phase information to determine a property of a surface of the sample from which the radiation is scattered.

16. Apparatus according to claim 14, wherein the sample comprises a semiconductor wafer, and wherein the signal processor is adapted to detect a defect on the surface of the wafer responsive to the amplitude and phase information.

* * * * *